United States Patent [19]

Adolphi et al.

[11] 4,061,762
[45] Dec. 6, 1977

[54] NAPHTH-[2,1-d]-ISOTHIAZOLE AND NEMATOCIDAL USES THEREOF

[75] Inventors: Heinrich Adolphi, Limburgerhof; Helmut Fleig, Mannheim; Helmut Hagen, Frankenthal, all of Germany

[73] Assignee: BASF Aktiengesellschaft, Ludwigshafen (Rhine), Germany

[21] Appl. No.: 704,561

[22] Filed: July 12, 1976

[51] Int. Cl.$^2$ .............. C07D 265/04; A61K 31/425

[52] U.S. Cl. .............. 424/270; 260/304 A
[58] Field of Search .............. 260/304 A; 424/270

Primary Examiner—R. J. Gallagher
Attorney, Agent, or Firm—Keil, Thompson & Shurtleff

[57] ABSTRACT

Naphth-[2,1-d]-isothiazole, agents for combatting nematodes containing this active ingredient, and a method of combatting nematodes with this active ingredient.

2 Claims, No Drawings

NAPHTH-[2,1-d]-ISOTHIAZOLE AND NEMATOCIDAL USES THEREOF

The present invention relates to naphth-[2,1-d]-isothiazole of the formula

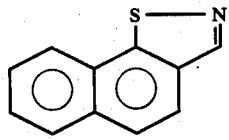

said nematocides containing this compound as active ingredient.

We have found that naphth-[2,1-d]-isothiazole has an excellent nematocidal action for instance on plant-parasitic root-knot nematodes, cyst eelworms and stem and leaf eelworms. The effectiveness of this compound is particularly surprising as its chemical structure bears no similarity to that of known nematocidal active ingredients. Compared with prior art active ingredients, naphth-[2,1-d]-isothiazole has the special advantage that it is hardly toxic and is well tolerated by plants.

Naphth-[2,1-d]-isothiazole may be prepared by the analogous processes described in German Pat. No. 1,670,196 and U.S. Pat. No. 3,682,941 by reaction of 1-halo-2-dihalomethylnaphthalene or 1-halo-2-formylnaphthalene with elementary sulfur and ammonia.

Naphth-2,1-d]-isothiazole is effective against nematodes such as root-knot nematodes, e.g., *Meloidogyne incognita, Meloidogyne hapla* and *Meloidogyne javanica*, cyst-forming nematodes, e.g., *Heterodera rostochiensis, Heterodera schachtii, Heterodera avenae, Heterodera glycines*, and *Heterodera trifolii*, and stem and leaf eelworms, e.g., *Ditylenchus dipsaci, Ditylenchus destructor, Pratylenchus neglactus, Pratylenchus penetrans, Paratylenchus goodeyi, Paratylenchus curvitatus, Tylenchorhynchus dubius, Tylenchorhynchus claytoni, Rotylenchus robustus, Heliocotylenchus multicintus, Radopholus similis, Belonolaimus longicaudatus, Longidorus elongatus*, and *Trichodorus primitivus*.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient of the invention.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products or sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The active ingredient concentration in the ready-to-use mix may vary over a wide range. It is generally from 0.0001 to 100%, preferably from 0.01 to 10%.

The active ingredient may also be successfully used in an ultra-low volume, making it possible to apply 95% formulations or even the pure active ingredient (100%).

The preparations are uniformly applied in amounts of from 1 to 100 kg of active ingredient per hectare, and then incorporated into the soil.

There may be added to the active ingredient oils of various types, herbicides, fungicides, insecticides, and bactericides, if desired immediately before use (tank-mix). These agents may be added to the agents of the invention in a weight ratio of from 1:10 to 10:1.

The following are examples of compounds which may be added:
1,2-dibromo-3-chloropropane
1,3-dichloropropene
1,3-dichloropropane + 1,2-dichloropropane
1,2-dibromoethane
2-sec-butyl-phenyl-N-methylcarbamate
o-chlorophenyl-N-methylcarbamate
3-isopropyl-5-methylphenyl-N-methylcarbamate o-isopropoxyphenyl-N-methylcarbamate
3,5-dimethyl-4-methylmercaptophenyl-N-methylcarbamate
4-dimethylamino-3,5-xylyl-N-methylcarbamate
2-(1,3-dioxolan-2-yl)-phenyl-N-methylcarbamate
1-naphthyl-N-methylcarbamate
2,3-dihydro-2,2-dimethylbenzofuran-7-yl-N-methylcarbamate
2,2-dimethyl-1,3-benzodioxol-4-yl-N-methylcarbamate
2-dimethylamino-5,6-dimethyl-4-pyrimidinyldimethylcarbamate
2-methyl-2-(methylthio)-propionaldehyde-O-(methylcarbamoyl)-oxime
S-methyl-N-[(methylcarbamoyl)-oxy]-thioacetimidate
methyl-N',N'-dimethyl-N-[(methylcarbamoyl)-oxy]-1-thiooxamidate
N-(2-methyl-4-chlorophenyl)-N',N'-dimethylformamidine tetrachlorothiophene
O,O-dimethyl-O-(p-nitrophenyl)-phosphorothioate
O,O-diethyl-O-(p-nitrophenyl)-phosphorothioate
O-ethyl-O-(p-nitrophenyl)-phenylphosphonothioate
O,O-dimethyl-O-(3-methyl-4-nitrophenyl)-phosphorothioate
O,O-diethyl-O-(2,4-dichlorophenyl)-phosphorothioate
O-ethyl-O-(2,4-dichlorophenyl)-phenylphosphonothioate
O,O-dimethyl-O-(2,4,5-trichlorophenyl)-phosphorothioate
O-ethyl-O-(2,4,5-trichlorophenyl)-ethylphosphonothioate
O,O-dimethyl-O-(4-bromo-2,5-dichlorophenyl)-phosphorothioate
O,O-dimethyl-O-(2,5-dichloro-4-iodophenyl)-phosphorothioate
O,O-dimethyl-O-(3-methyl-4-methylthiophenyl)-phosphorothioate
O-ethyl-O-(3-methyl-4-methylthiophenyl)-isopropylphosphoroamidate
O,O-diethyl-O-[p-(methylsulfinyl)-phenyl]-phosphorothioate
O-ethyl-S-phenylethylphosphonodithioate
O,O-diethyl-[2-chloro-1-(2,4-dichlorophenyl)-vinyl]-phosphate
O,O-dimethyl-[2-chloro-1-(2,4,5-trichlorophenyl)]-vinylphosphate
O,O-dimethyl-S-(1-phenyl)-ethylacetate phosphorodithioate bis-(dimethylamino)-fluorophosphine oxide
octamethylpyrophosphoramide
O,O,O,O-tetraethyldithiopyrophosphate
S-chloromethyl-O,O-diethylphosphorodithioate
O-ethyl-S,S-dipropylphosphorodithioate
O,O-dimethyl-O-2,2-dichlorovinylphosphate
O,O-dimethyl-1,2-dibromo-2,2-dichloroethylphosphate
O,O-dimethyl-2,2,2-trichloro-1-hydroxyethylphosphonate
O,O-dimethyl-S-[1,2-biscarbethoxyethyl-(1)]-phosphorodithioate
O,O-dimethyl-O-(1-methyl-2-carbomethoxyvinyl)-phosphate
O,O-dimethyl-S-(N-methylcarbamoylmethyl)-phosphorodithioate
O,O-dimethyl-S-(N-methylcarbamoylmethyl)-phosphorothioate
O,O-dimethyl-S-(N-methoxyethylcarbamoylmethyl)-phosphorodithioate
O,O-dimethyl-S-(N-formyl-N-methylcarbamoylmethyl)-phosphorodithioate
O,O-dimethyl-O-[1-methyl-2-(methylcarbamoyl)-vinyl]-phosphate
O,O-dimethyl-O-[(1-methyl-2-dimethylcarbamoyl)-vinyl]-phosphate
O,O-dimethyl-O-[(1-methyl-2-chloro-2-diethylcarbamoyl)-vinyl]-phosphate
O,O-dimethyl-S-(ethylthiomethyl)-phosphorodithioate
O,O-diethyl-S-[(p-chlorophenylthio)-methyl]-phosphorodithioate
O,O-dimethyl-S-(2-ethylthioethyl)-phosphorothioate
O,O-dimethyl-S-(2-ethylthioethyl)-phosphorodithioate
O,O-dimethyl-S-(2-ethylsulfinylethyl)-phosphorothioate
O,O-diethyl-S-(2-ethylthioethyl)-phosphorodithioate
O,O-dimethyl-S-(2-ethylsulfinylethyl)-phosphorothioate
O,O-diethyl-thiophosphoryliminophenylacetonitrile
O,O-diethyl-S-(2-chloro-1-phthalimidoethyl)-phosphorodithioate
O,O-diethyl-S-[6-chlorobenzoxazolon-(2)-yl-(3)]-methyldithiophosphate
O,O-dimethyl-S-[2-methoxy-1,3,4-thiodiazol-5-onyl-(4)-methyl]-phosphorodithioate
O,O-diethyl-O-[3,5,6-trichloropyridyl(2)]-phosphorothioate
O,O-diethyl-O-(2-pyrazinyl)-phosphorothioate
O,O-diethyl-O-[2-isopropyl-4-methylpyrimidinyl-(6)]-phosphorothioate
O,O-diethyl-O-[2-(diethylamino)-6-methyl-4-pyrimidinyl]-thionophosphate
O,O-dimethyl-S-(4-oxo-1,2,3-benzotriazin-3-ylmethyl)-phosphorodithioate
O,O-dimethyl-S-[(4,6-diamino-1,3,5-triazin-2-yl)-methyl]-phosphorodithioate
O,O-diethyl-(1-phenyl-1,24-triazol-3-yl)-thionophosphate
O,S-dimethylphosphoroamidothioate
O,S-dimethyl-N-acetylphosphoroamidothioate
γ-hexachlorocylcohexane
1,1-di-(p-methoxyphenyl)-2,2,2-trichloroethane
6,7,8,9,10,10-hexachloro-1,5,5a,6,9,9a-hexahydro-6,9-methano-2,4,3-benzodioxathiepine-3-oxide.

The following examples demonstrate the preparation and use of the new active ingredient, and the manufacture of nematocides containing napth-[2,1-d]-isothiazole as well as active ingredient.

EXAMPLE 1

In a tantalum autoclave, 95 parts by weight of 1-chloro-2-formylnaphthalene, 16 parts by weight of sulfur and 250 parts by weight of ammonia in 500 parts by weight of methanol are heated for 20 hours at 90° C. After the solvent has been distilled off, the reaction mixture is washed with water, dried, and distilled in vacuo. There is obtained 68.5 parts by weight (74% of theory) of naphth--[2,1-d]-isothiazole, m.p. 52° C.

EXAMPLE 2

Action on root-knot nematodes (*Meloidogyne incognita*)

Young tomato plants are each planted in 500 g of compost infested to a considerable extent with root-knot nematodes.

After 3 days the plants are treated with 30 ml of an aqueous active ingredient preparation.

After 6 to 8 weeks the roots are examined with regard to gall formation. No galls are formed when an active ingredient preparation containing 0.1 wt% of naphth-[2,1-d]-isothiazole is used.

EXAMPLE 3

Action on root-know nematodes (*Meloidogyne incognita*)

Compost infested to a considerable extent with nematodes is thoroughly mixed with active ingredient preparations to give a final active ingredient concentration of 10 or 25 ppm.

After storage for 10 days in the greenhouse 500 g of compost is filled into flowerpots, in which young tomato plants are planted or cucumber seeds sown (2 per pot). After 8 and 6 weeks respectively the roots of the plants are investigated with regard to galls. In the soil containing 10 ppm of active ingredient odd galls still appear, whereas in the soil containing 25 ppm of active ingredient no galls are observed.

EXAMPLE 4

Action on root-knot nematodes (*Meloidogyne incognita*)

The roots of tomato plants grown in sterilized soil are dipped for one hour in an aqueous active ingredient preparation, and the plants are then replanted in soil infested with root-knot nematodes.

After 6 to 8 weeks no galls have formed on the roots treated with a 0.1 wt.% active ingredient preparation.

EXAMPLE 5

Action on sugar-beet nematodes (*Heterodera schachtii*)

Soil infested to a considerable extent with sugar-beet nematodes is carefully mixed with the active ingredient, and subsequently the mixtures are filled into 4-chamber vessels of transparent plastic. Four seeds of the "Diamant" rape variety are then placed in each vessel. The volume of the vessels is 200 cm³.

The comparative agent is 2,3-dihydro-2,2-dimethyl-benzofuran-7-yl-N-methylcarbamate. After 8 weeks the roots of the plants are investigated with regard to nematode cysts.

| Active ingredient | Amount of active ingredient in soil | Evaluation |
| --- | --- | --- |
| Naphth-[2,1-d]-isothiazole | 25 ppm | no cysts |
| Comparative agent | 100 ppm | no cysts |
|  | 50 ppm | isolated cysts |
|  | 25 ppm | numerous cysts |

EXAMPLE 6

Action on saprophytic soil nematodes 500 g of compost is intimately mixed with the active ingredient and the mixture is stored moist in pots for 10 days.

100 g samples are then filled into gauze bags, which are then placed in funnels equipped with a tube and pinchcock. The funnel is carefully filled with water until the bag is completely covered. After 24 hours 2 ml of water is let out at the pinchcock and investigated as to the presence of nematodes. At a concentration of 100 ppm of naphth-[2,1-d]-isothiazole in the soil no living nematodes can be detected.

We claim:

1. Naphth-[2,1-d]-isothiazole of the formula

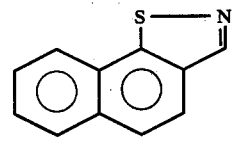

2. A process for combatting nematodes, wherein the soil in which the nematodes live is treated with a nematode-toxic amount of naphth-[2,1-d]-isothiazole.